(12) United States Patent
Hatano et al.

(10) Patent No.: US 10,136,800 B2
(45) Date of Patent: Nov. 27, 2018

(54) BENDING OPERATION DEVICE AND ENDOSCOPE

(71) Applicant: OLYMPUS CORPORATION, Tokyo (JP)

(72) Inventors: Keisuke Hatano, Koganei (JP); Kiwamu Fujitani, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/486,944

(22) Filed: Apr. 13, 2017

(65) Prior Publication Data

US 2017/0215697 A1 Aug. 3, 2017

Related U.S. Application Data

(63) Continuation of application No. PCT/JP2015/078766, filed on Oct. 9, 2015.

(30) Foreign Application Priority Data

Mar. 18, 2015 (JP) ................................. 2015-055174

(51) Int. Cl.
*A61B 1/00* (2006.01)
*A61B 1/005* (2006.01)
(Continued)

(52) U.S. Cl.
CPC .......... *A61B 1/0052* (2013.01); *A61B 1/0057* (2013.01); *G02B 23/24* (2013.01); *A61B 1/00066* (2013.01); *A61B 1/04* (2013.01)

(58) Field of Classification Search
CPC ..... A61B 1/0052; A61B 1/0057; A61B 1/005; A61B 1/00066; A61B 1/0051; A61B 1/0055; A61B 1/008
See application file for complete search history.

(56) References Cited

U.S. PATENT DOCUMENTS 5,626,553 A * 5/1997 Frassica ............... A61B 1/0052
600/146

FOREIGN PATENT DOCUMENTS

EP 2 805 664 A1 11/2014
JP 64-5523 A 1/1989
(Continued)

OTHER PUBLICATIONS

International Search Report dated Jan. 12, 2016 received in PCT/JP2015/078766.
(Continued)

*Primary Examiner* — Timothy J Neal
(74) *Attorney, Agent, or Firm* — Scully, Scott, Murphy & Presser, P.C.

(57) ABSTRACT

A bending operation device, includes: a bending lever that is inclinably supported with respect to an operation section of an endoscope; an arm part that is provided in the bending lever and includes a distal end displaceable in conjunction with inclination operation of the bending lever; and an intermediate lever that is swingably supported with respect to the operation section, includes a force point at a middle of the intermediate lever, and includes a point of application at a position farther from a fulcrum (a shaft portion) than the force point, the force point being connected to the distal end of the arm part through an intermediate wire, and the point of application being connected to a bending wire.

5 Claims, 10 Drawing Sheets

(51) Int. Cl.
*G02B 23/24* (2006.01)
*A61B 1/04* (2006.01)

(56) References Cited

FOREIGN PATENT DOCUMENTS

| | | |
|---|---|---|
| JP | 2001-384 A | 1/2001 |
| JP | 2003-325437 A | 11/2003 |
| JP | 2004-321492 A | 11/2004 |
| JP | 2004-321697 A | 11/2004 |
| JP | 2008-35882 A | 2/2008 |
| JP | 2009-101076 A | 5/2009 |
| WO | 2014/123245 A1 | 8/2014 |

OTHER PUBLICATIONS

Japanese Office Action dated Oct. 18, 2016 received in JP Application No. 2016-544634.
Extended Supplementary European Search Report dated Jun. 4, 2018 in European Patent Application No. 15 88 5549.4.

* cited by examiner

BENDING OPERATION DEVICE AND ENDOSCOPE

CROSS REFERENCE TO RELATED APPLICATION

This application is a continuation application of PCT/JP2015/078766 filed on Oct. 9, 2015 and claims benefit of Japanese Application No. 2015-055174 filed in Japan on Mar. 18, 2015, the entire contents of which are incorporated herein by this reference.

BACKGROUND OF INVENTION

1. Field of the Invention

The present invention relates to a bending operation device that bends a bending portion in conjunction with inclination operation of a bending lever, and to an endoscope.

2. Description of the Related Art

An endoscope insertable into a subject or an object has been widely used to allow for observation of a point inside the subject or the object that is difficult to be observed, for example, in-vivo in a medical field or an inside of a structure in an industrial field.

An insertion section of such an endoscope is provided with a bending portion that improves insertion property and observation property in the subject or the object. The bending portion is bent by a bending operation device provided in an operation section.

For example, Japanese Patent Application Laid-Open Publication No. 2003-325437 discloses a joystick bending operation device as the bending operation device to bend the bending portion of the insertion section. The bending operation device of the kind includes a joystick bending lever in which a plurality of arm parts are fixed to a proximal end portion, and the bending operation device bends the bending portion by pulling or relaxing traction wires that are respectively coupled to ends of the respective arm parts, in conjunction with the inclination operation of the bending lever.

SUMMARY OF THE INVENTION

An bending operation device according to an aspect of the present invention includes: a bending lever that is inclinably supported with respect to an operation section of an endoscope; an arm part that is provided in the bending lever and includes a distal end displaceable in conjunction with inclination operation of the bending lever; and an intermediate lever, in which the intermediate lever includes a fixed end that is swingably supported with respect to the operation section, includes a force point at a middle of the intermediate lever, and includes a point of application at a position that is farther from a fulcrum than the force point and is closer to a free end than the force point in a longitudinal direction of the intermediate lever, the force point being connected to the distal end of the arm part through an intermediate member, the point of application being connected to a bending wire, and the bending wire bending a bending portion provided in an insertion section of the endoscope.

In addition, an endoscope according to an aspect of the present invention includes the above-described bending operation device in the above-described operation section.

DETAILED DESCRIPTION OF THE PREFERRED EMBODIMENT(S)

Figure 1:
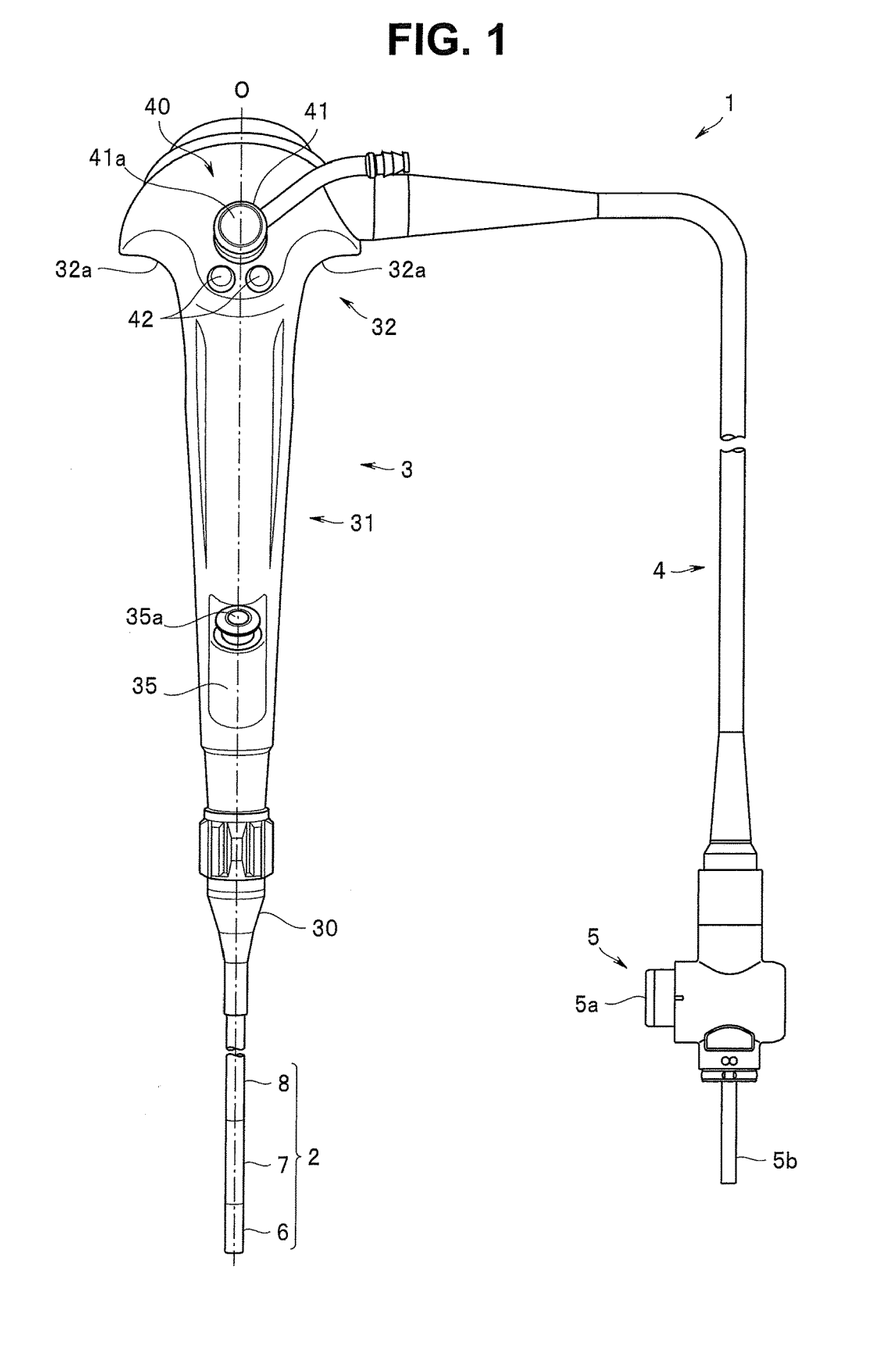
FIG. 1 is a front view illustrating an appearance of an endoscope.
Figure 2:
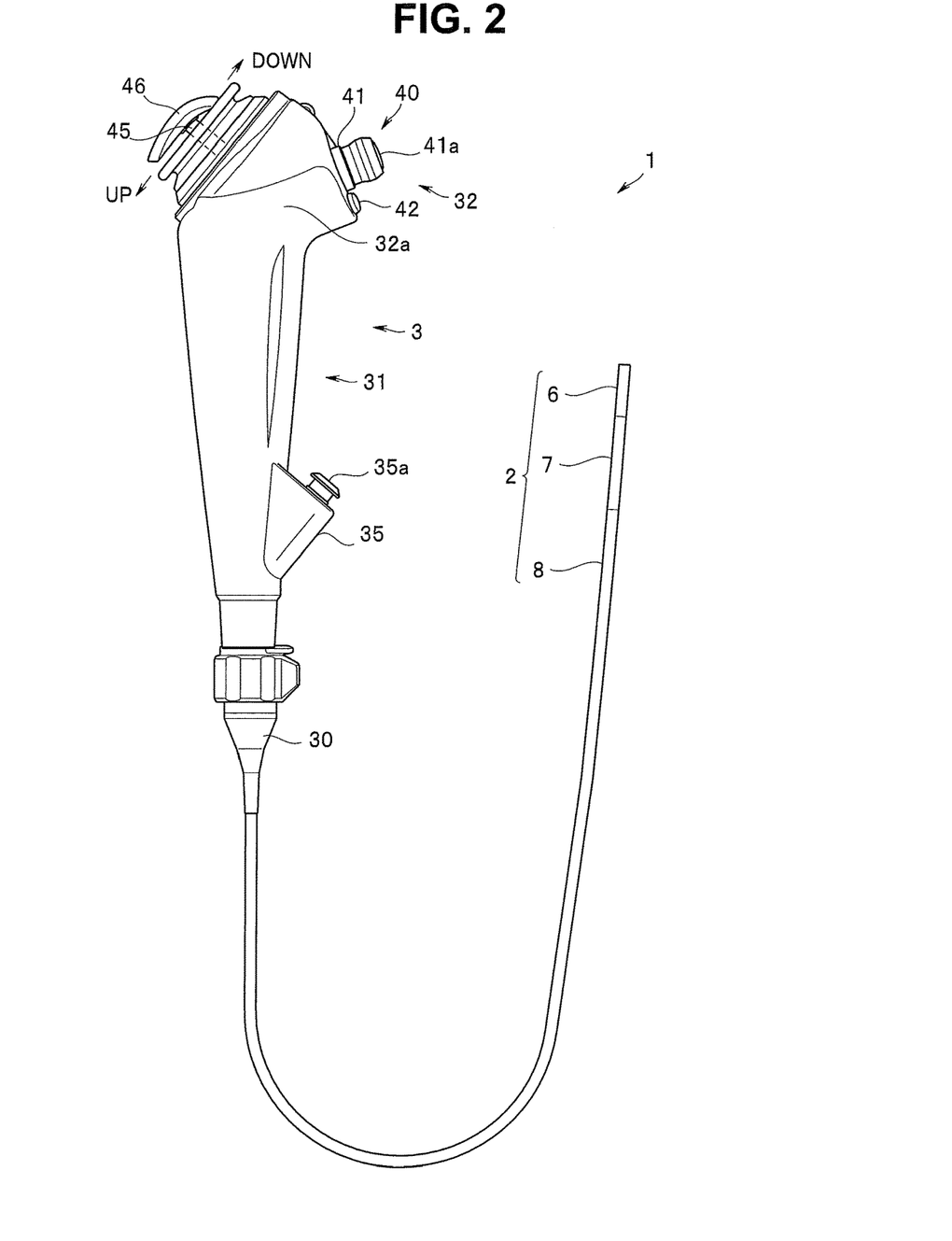
FIG. 2 is a right side view illustrating the appearance of the endoscope.
Figure 3:
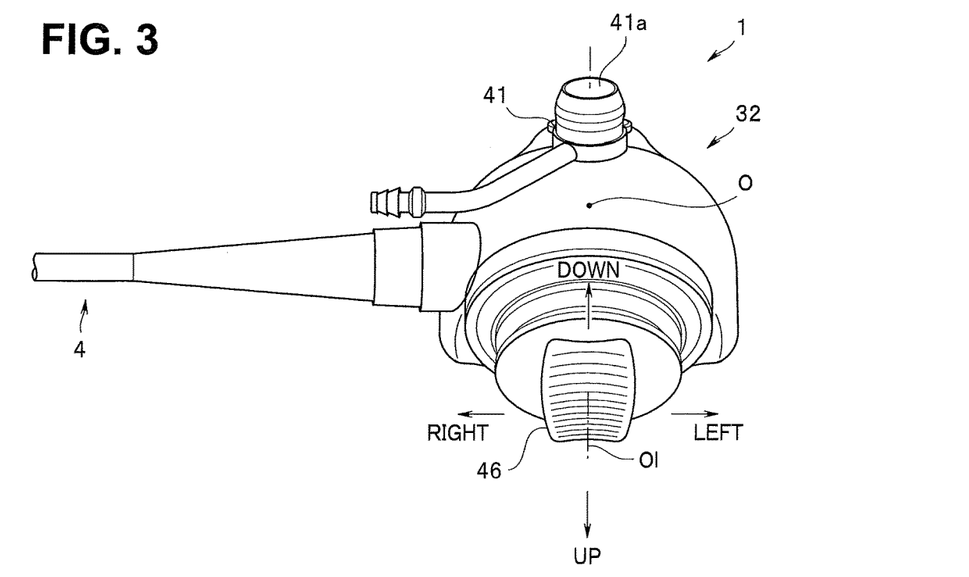
FIG. 3 is a top view illustrating the appearance of the endoscope.
Figure 4:
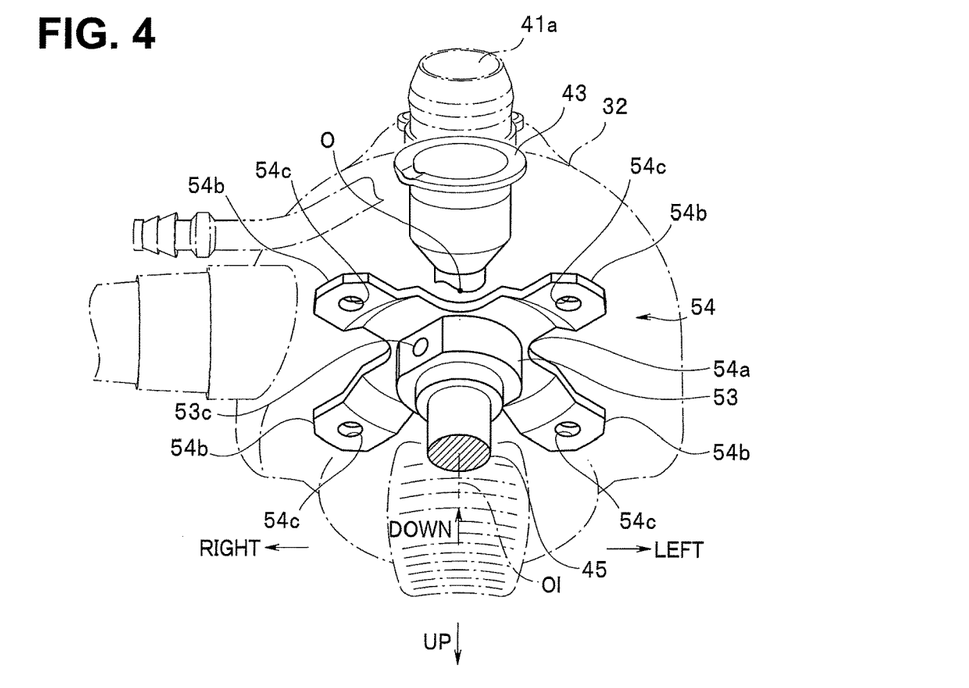
FIG. 4 is an explanatory diagram illustrating positional relationship between a wire traction member and a cylinder.
Figure 5:
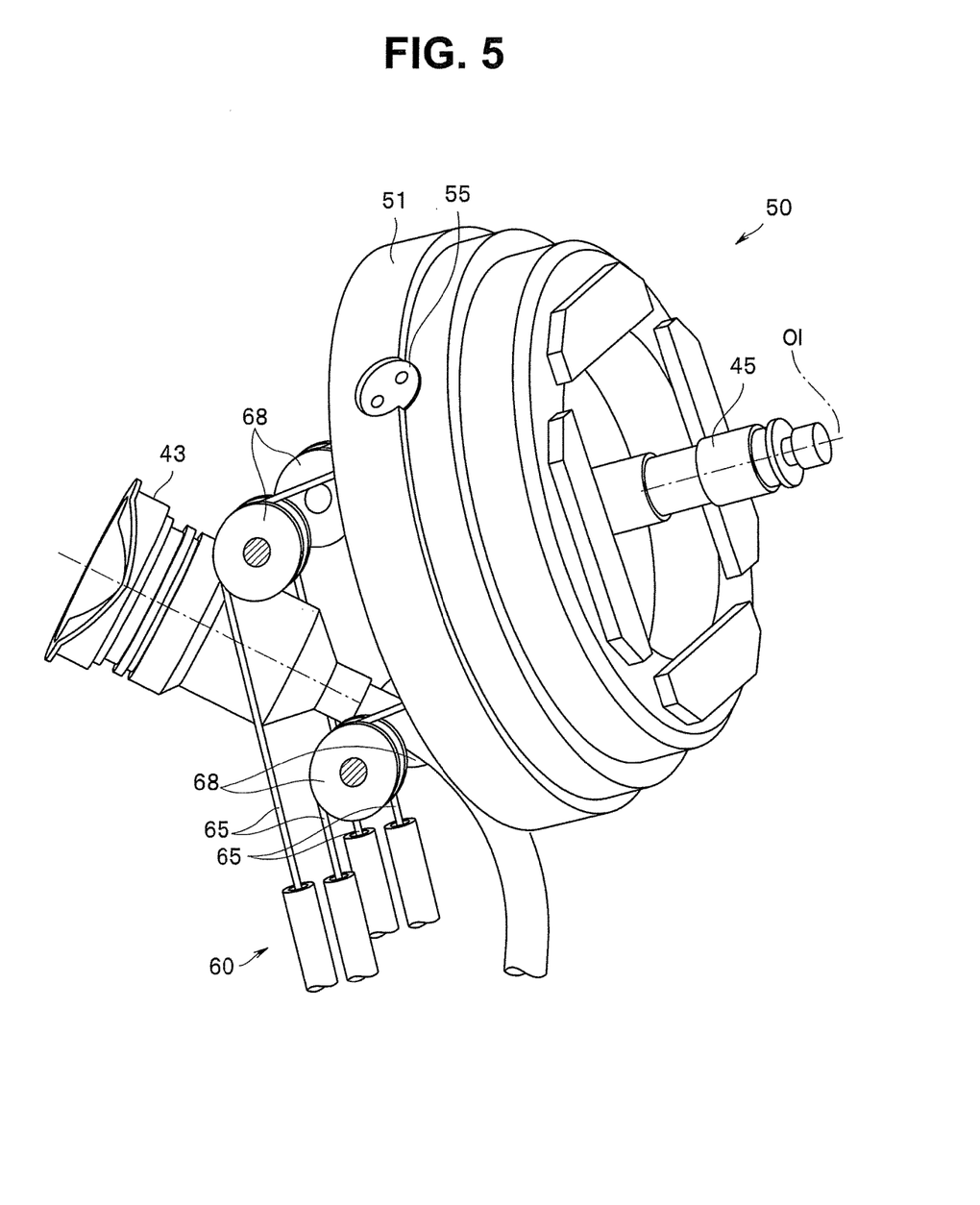
FIG. 5 is a perspective view illustrating positional relationship between a wire traction mechanism and the cylinder.
Figure 6:
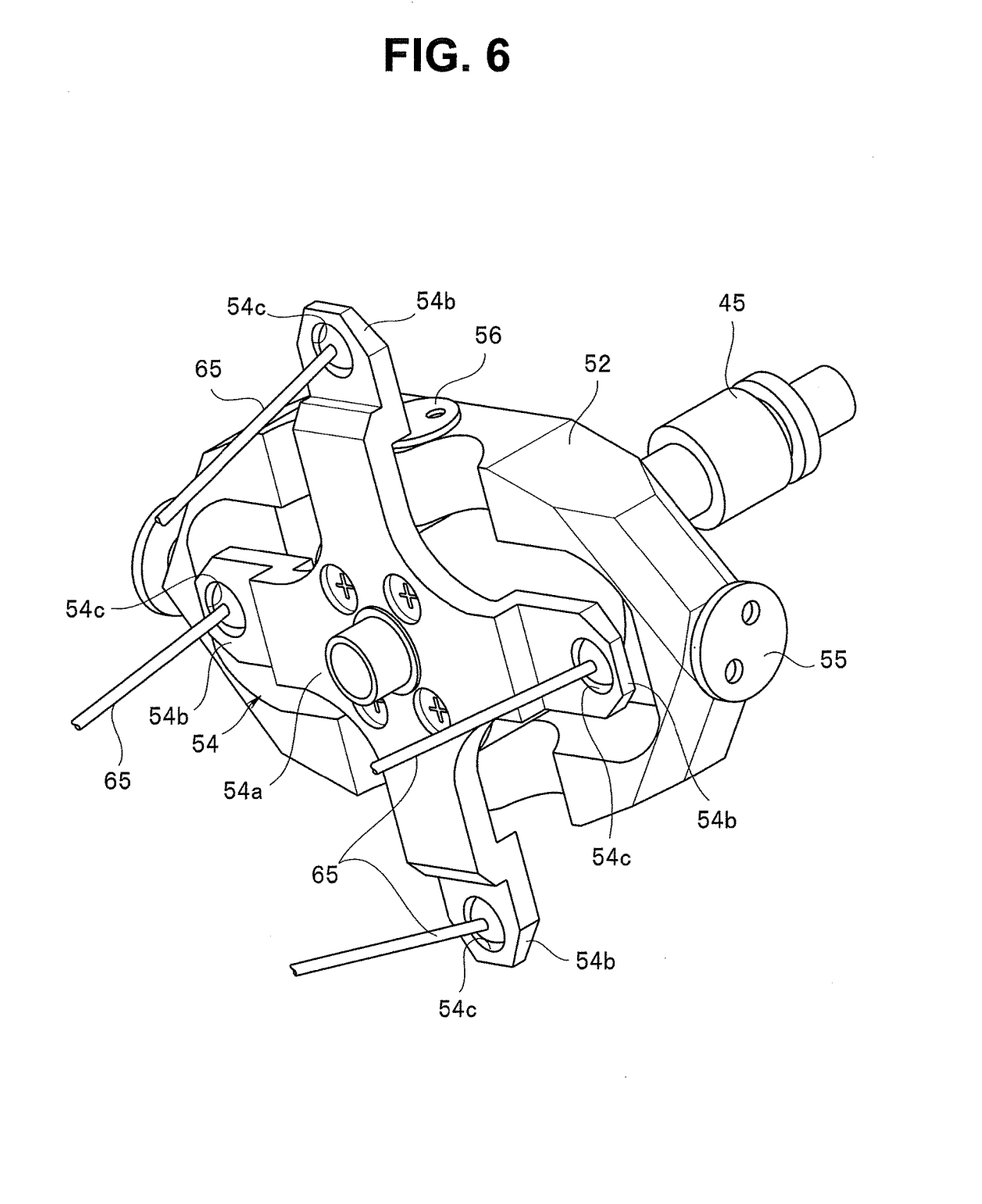
FIG. 6 is a perspective view illustrating an internal structure of the wire traction mechanism.
Figure 7:
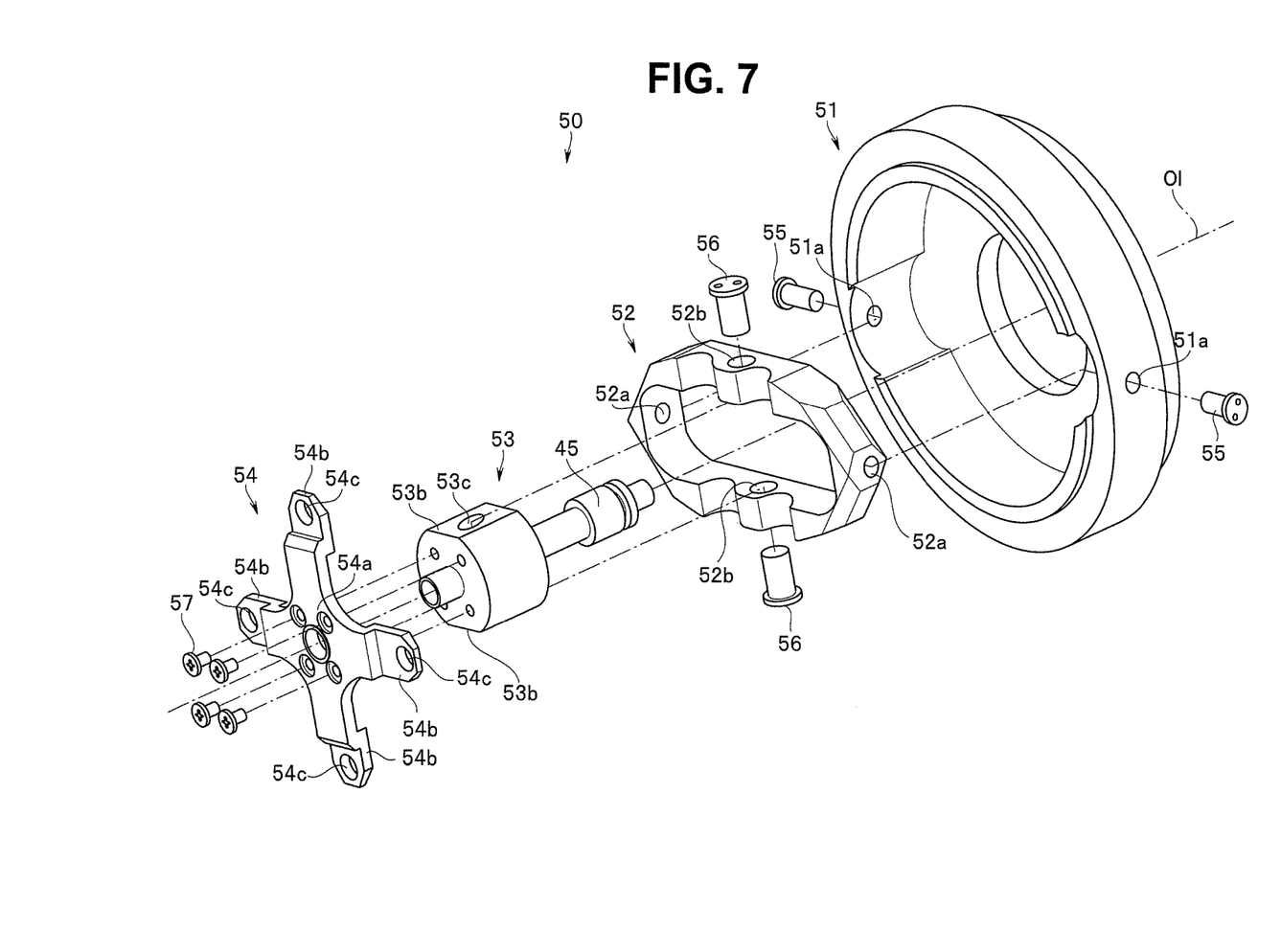
FIG. 7 is an exploded perspective view illustrating the internal structure of the wire traction mechanism.
Figure 8:
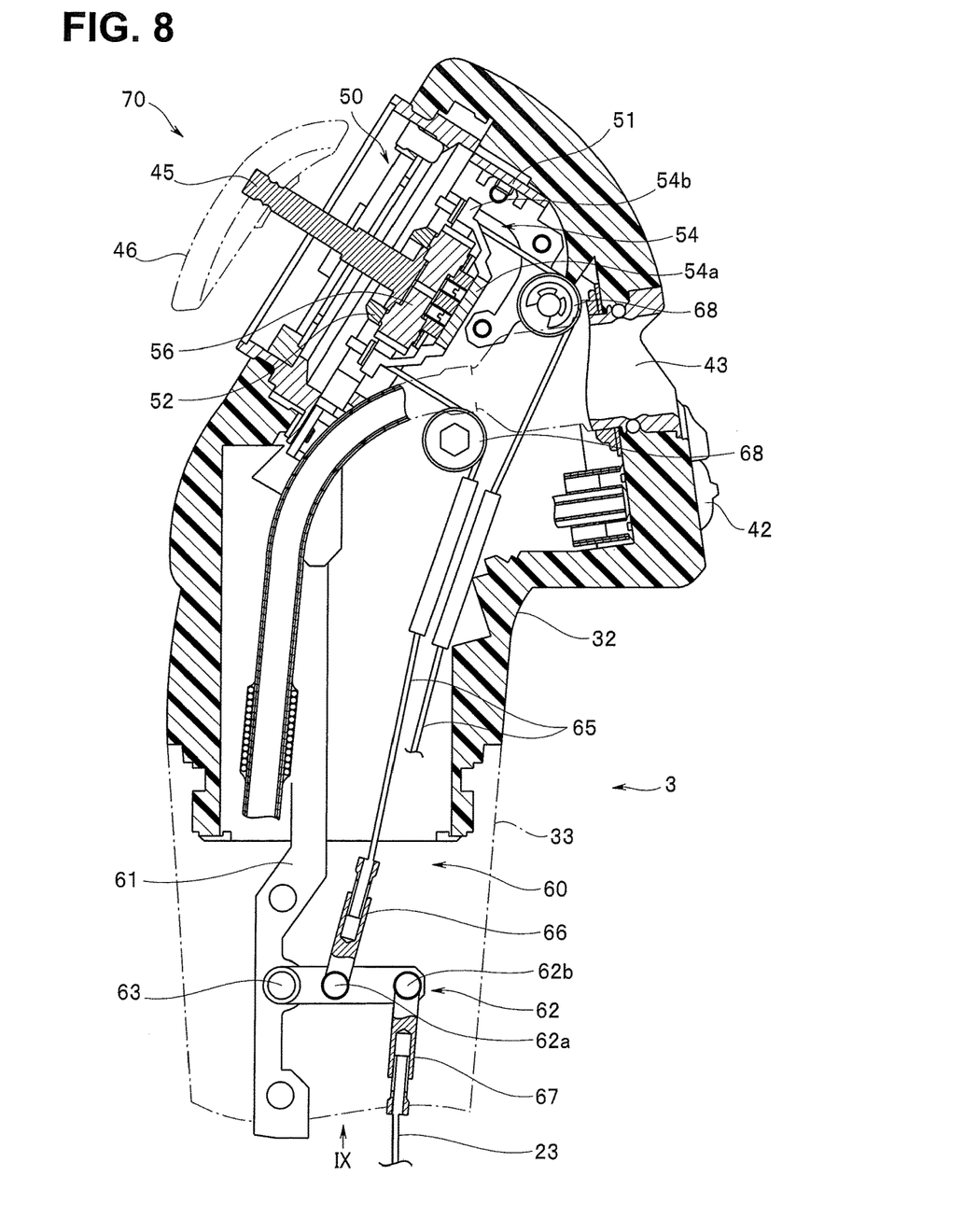
FIG. 8 is a cross-sectional diagram illustrating a main part of an operation section.
Figure 9:
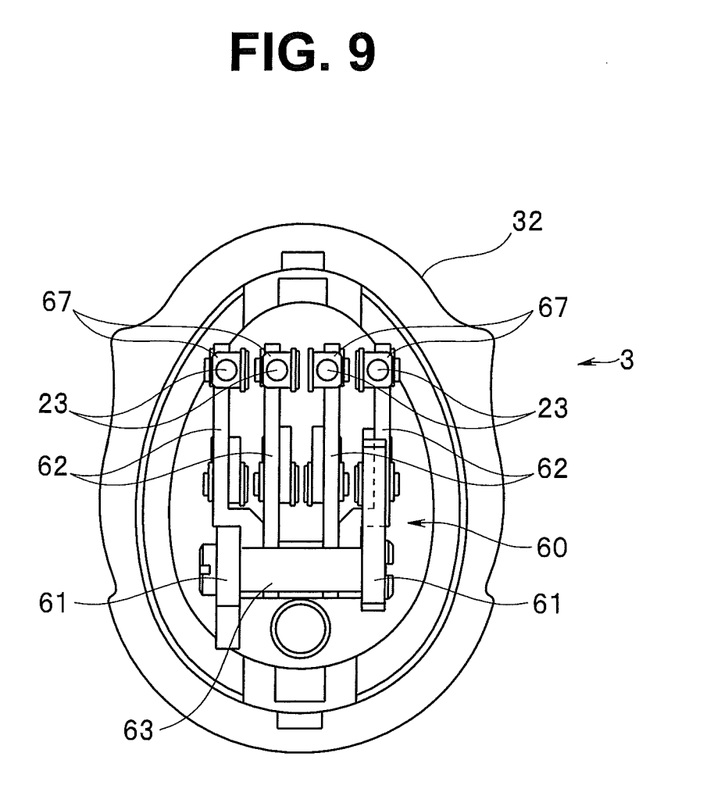
FIG. 9 is a diagram as viewed from arrow IX in FIG. 8.
Figure 10:
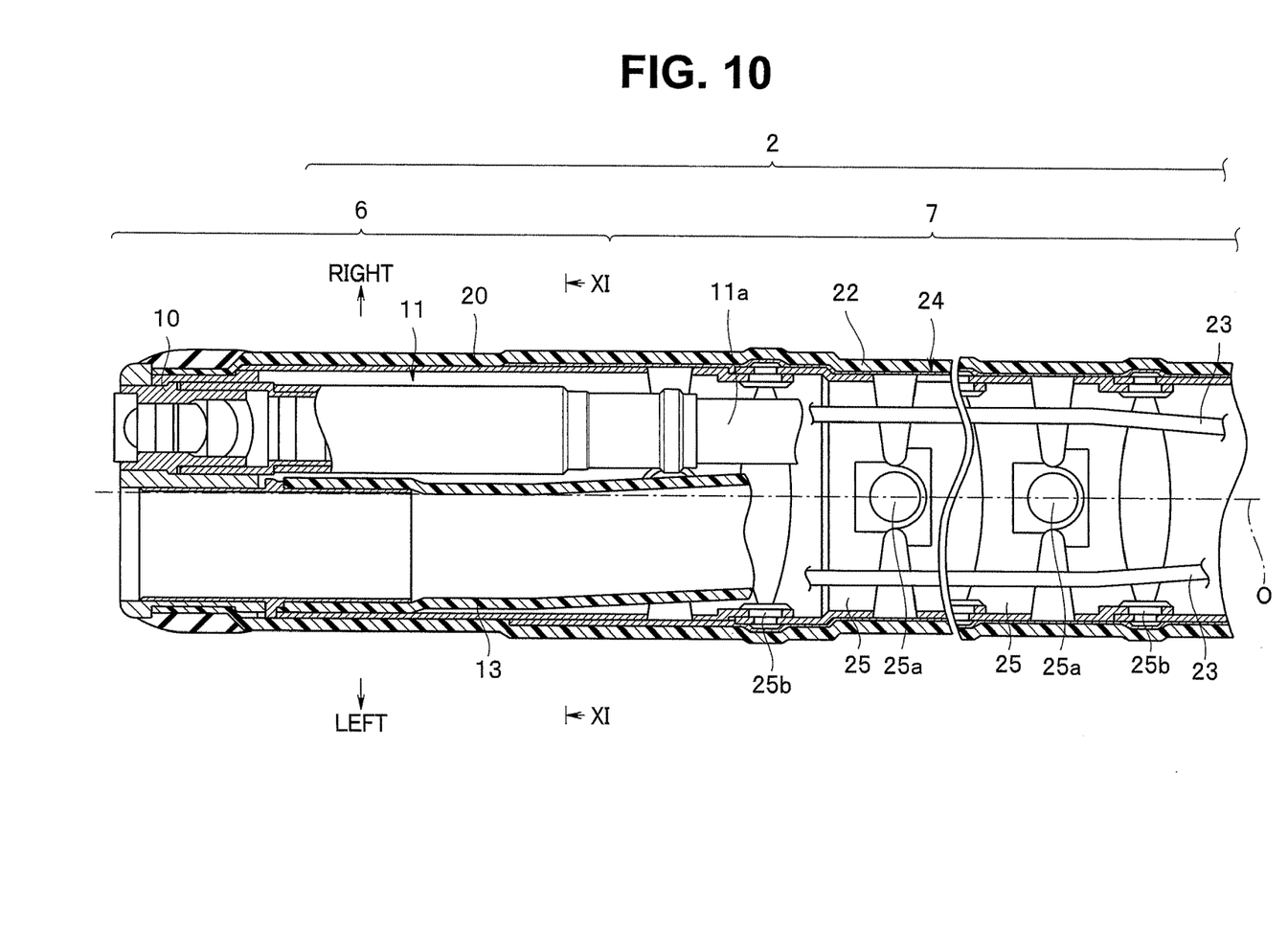
FIG. 10 is a cross-sectional diagram illustrating a main part of a distal end portion and a bending portion.
Figure 11:
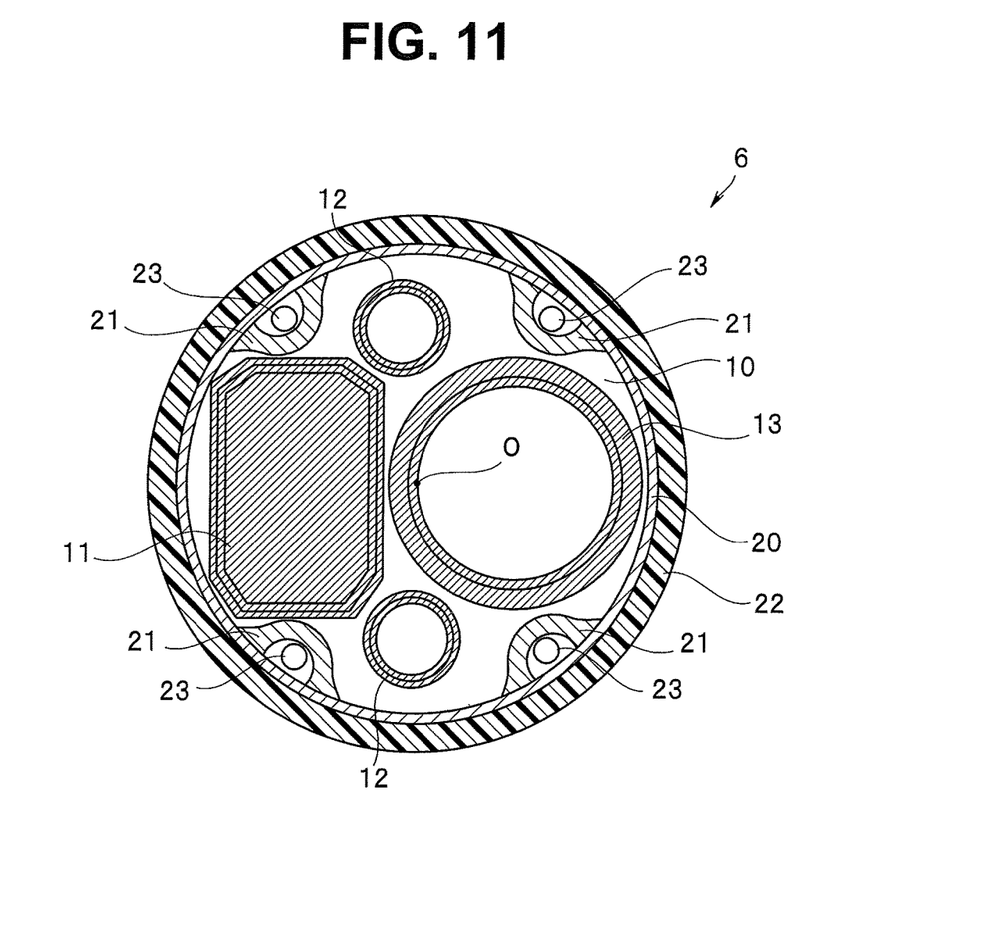
FIG. 11 is a cross-sectional diagram illustrating the distal end portion taken along line XI-XI in FIG. 10.

An embodiment of the present invention is described below with reference to drawings. The drawings relate to an embodiment of the present invention. FIG. 1 is a front view illustrating an appearance of an endoscope. FIG. 2 is a right side view illustrating the appearance of the endoscope. FIG. 3 is a top view illustrating the appearance of the endoscope. FIG. 4 is an explanatory diagram illustrating positional relationship between a wire traction member and a cylinder. FIG. 5 is a perspective view illustrating positional relationship between a wire traction mechanism and the cylinder. FIG. 6 is a perspective view illustrating an internal structure of the wire traction mechanism. FIG. 7 is an exploded perspective view illustrating the internal structure of the wire traction mechanism. FIG. 8 is a cross-sectional diagram illustrating a main part of an operation section. FIG. 9 is a diagram as viewed from arrow IX in FIG. 8. FIG. 10 is a cross-sectional diagram illustrating a main part of a distal end portion and a bending portion. FIG. 11 is a cross-sectional diagram illustrating the distal end portion taken along line XI-XI in FIG. 10.

As illustrated in FIGS. 1 and 2, an endoscope 1 according to the present embodiment is an endoscope for bronchi. The endoscope 1 includes: an insertion section 2 formed in an elongated tube shape; an operation section 3 that is connected to a proximal end of the insertion section 2; a universal cord 4 that is an endoscope cable extended from the operation section 3; and an endoscope connector 5 that is provided at a distal end of the universal cord 4.

The insertion section 2 is configured of a flexible tubular member in which a distal end portion 6, a bending portion 7, and a flexible tube portion 8 are connected in order from distal end side.

For example, as illustrated in FIGS. 10 and 11, a metal distal end rigid portion 10 is provided inside the distal end portion 6. An image pickup unit 11 in which an image pickup device such as a CCD and a CMOS is incorporated, a pair of light guides 12, and a treatment instrument insertion channel 13 are held by the distal end rigid portion 10.

In addition, a distalmost end bending piece 20 that has a substantially cylindrical shape is externally fitted to the proximal end of the distal end rigid portion 10, and an outer periphery of the distalmost end bending piece 20 is covered with a bending rubber 22, inside the distal end portion 6. A wire fixing portion 21 is provided at four positions around an insertion shaft O on an inner periphery of the distalmost end bending piece 20, and distal ends of four traction wires 23 that are inserted into the insertion section 2 are respectively fixed to the wire fixing portions 21.

Here, to efficiently dispose the respective components without increasing a diameter of the distal end portion 6, the image pickup unit 11 and the treatment instrument insertion channel 13 that are large members are arranged side by side in the distal end rigid portion 10 and the distalmost end bending piece 20 (see FIGS. 10 and 11), and the light guides 12 are respectively disposed in an upper space and a lower space that are formed by the arrangement.

Further, to avoid interference of the image pickup unit 11 and the treatment instrument insertion channel 13 with the respective traction wires 23, the wire fixing portions 21 are provided at respective positions that are rotated around the insertion shaft O by a predetermined angle respectively from upper, lower, right, and left positions of the distal end portion 6. In other words, for example, as illustrated in FIG. 11, the wire fixing portions 21 are respectively provided to the distalmost end bending piece 20 at positions that are rotated around the insertion shaft O in right and left directions within a range of 30 degrees to 60 degrees from the up direction of the distal end portion 6 and at positions that are rotated around the insertion shaft O in right and left directions within a range of 30 degrees to 60 degrees from the down direction of the distal end portion 6.

The bending portion 7 is configured to be actively bent in all directions including up-down/right-left directions around the insertion shaft O, in response to operation input to the operation section 3 by an operator or other person. In other words, the bending portion 7 according to the present embodiment includes bending piece set 24 in which a plurality of bending pieces 25 are coupled with one another alternately through pivot parts 25a and pivot parts 25b. The pivot parts 25a are disposed in the up-down direction of the insertion section 2, and the pivot parts 25b are disposed in the right-left direction of the insertion section 2.

A signal cable 11a, the light guides 12, and the treatment instrument insertion channel 13 that are disposed in a manner similar to the inside of the distal end portion 6 are inserted into the bending piece set 24. The signal cable 11a is extended from the image pickup unit 11. In addition, wire guides (not illustrated) into which the traction wires 23 are respectively inserted are provided, in the predetermined bending pieces 25 that configure the bending piece set 24, at positions that are substantially similar in rotation position around the insertion shaft O to the above-descried respective wire fixing portions 21. Further, an outer periphery of the bending piece set 24 is covered with the bending rubber 22 that is extended from the distal end portion 6 side.

The flexible tube portion 8 is configured of a flexible tubular member that is passively bendable. The signal cable 11a, the light guides 12, and the treatment instrument insertion channel 13 mentioned above (not illustrated here) are inserted into the flexible tube portion 8.

The operation section 3 includes: a bend preventing portion 30 that is connected to the flexible tube portion 8 while covering a proximal end of the flexible tube portion 8; a grasping portion 31 that is connected to the bend preventing portion 30 and is grasped by a hand of a user or the like; and an operation section body 32 that is connected to proximal end side of the grasping portion 31. Note that, in the present embodiment, directions around the insertion shaft O in the operation section 3 or the like are defined based on a state in which the user or the like grasps the grasping portion 31. More specifically, front-rear/right-left directions (a front surface, a rear surface, right and left side surfaces, and other surfaces) based on the user or the like grasping the grasping portion 31 are defined in the operation section 3.

As illustrated in FIG. 1, the grasping portion 31 is formed in a shape right-left symmetrical to the insertion shaft O (a center axis), which allows the user or the like to grasp the grasping portion 31 by any of a right hand and a left hand in the same way.

In addition, a treatment instrument insertion portion 35 is provided on a front surface on the distal end side of the grasping portion 31. The treatment instrument insertion portion 35 includes a treatment instrument insertion opening 35a into which treatment instruments for respective positions (not illustrated) are inserted. The treatment instrument insertion channel 13 communicates with the treatment instrument insertion opening 35a through an unillustrated branch member in the operation section 3. Further, a forceps plug (not illustrated) that is a lid member to close the treatment instrument insertion opening 35a is detachably attached to the treatment instrument insertion portion 35.

The operation section body 32 is configured of a hollow member that is formed in a substantially partial spherical shape swelling mainly toward right and left sides and front side, on the proximal end side of the grasping portion 31. An operation button group 40 for execution of various kinds of functions of the endoscope 1 is provided on the front surface of the operation section body 32. In contrast, a bending lever 45 serving as an operation lever for bending operation of the bending portion 7 is disposed on a rear surface of the operation section body 32. Moreover, the universal cord 4 is extended from one side part (for example, a left side part) of the operation section body 32.

In this case, the operation section body 32 has a shape that swells right-left symmetrically to the insertion shaft O. A guiding recessed portion 32a that guides, to the operation button group 40, an index finger or the like of the user grasping the grasping portion 31 is provided on each of the right and left side surfaces on the distal end side of the operation section body 32.

The universal cord 4 is a composite cable. The universal cord 4 passes through the inside of the insertion section 2 and reaches the operation section 3 from the distal end portion 6 side. In addition, the various kinds of signal lines extended from the operation section 3, the light guides 12 of a light source apparatus (not illustrated), and an air/water feeding tube extended from an air/water feeding apparatus (not illustrated) are inserted into the universal cord 4.

The endoscope connector 5 includes, on a side surface part, an electric connector portion 5a to which a signal cable that connects the endoscope 1 to a video processor (not illustrated) as an external apparatus is connected. The endoscope connector 5 further includes a light source connector portion 5b to which the light guides and an electric cable that connect the endoscope 1 to the light source apparatus as an external apparatus are connected.

Next, configurations of the respective portions in the operation section body 32 are described in more detail.

As illustrated in FIG. 1, the operation button group 40 includes, for example, a suction button 41a and two button switches 42. The suction button 41a projects from a suction valve 41 that is detachably attached to the operation section body 32. The two button switches 42 are allocated with optional functions among the various functions related to the endoscope 1.

The suction button 41a and the button switches 42 are right-left symmetrically disposed on the front surface of the operation section body 32. In other words, in the present embodiment, the suction button 41a is so disposed at a center of the operation section body 32 in a right-left width direction as to be overlapped with the insertion shaft O. In addition, the two button switches 42 are disposed at right-left symmetrical positions with the insertion shaft O in between, on the distal end side of the suction button 41a.

Here, for example, as illustrated in FIG. 4, a cylinder 43 that is connected to the suction valve 41 is provided inside the operation section body 32. The suction valve 41 is detachably attached to the cylinder 43, and the cylinder 43 is so disposed at the center of the operation section body 32 in the right-left width direction as to be overlapped with the insertion shaft O, correspondingly to the arrangement of the suction button 41a.

The bending lever 45 is configured of, for example a joystick lever that is inclinable in all directions including up-down/right-left directions. The bending lever 45 is disposed at a right-left symmetrical position on the rear surface of the operation section body 32. In other words, in the present embodiment, the bending lever 45 is so disposed at the center of the operation section body 32 in the right-left width direction as to be overlapped with the insertion shaft O. Here, for example, as illustrated in FIG. 3, as for the inclination direction of the bending lever 45, the right-left width direction of the operation section 3 that is orthogonal to the insertion shaft O is defined as the right-left direction of the inclination operation, and a direction orthogonal to the right-left width direction is defined as the up-down direction of the inclination operation.

More specifically, as for the inclination direction of the bending lever 45 according to the present embodiment, for example, the left side on the sheet in FIG. 3 is defined as an inclination direction (a left inclination direction) to bend the bending portion 7 leftward, the right side on the sheet in FIG. 3 is defined as an inclination direction (a right inclination direction) to bend the bending portion 7 rightward, the lower side on the sheet in FIG. 3 is defined as an inclination direction (an up inclination direction) to bend the bending portion 7 upward, and the upper side on the sheet in FIG. 3 is defined as an inclination direction (a down inclination direction) to bend the bending portion 7 downward.

A protrusion end part of the bending lever 45 is provided with a finger contact part 46 to which a thumb or the like of the user or the like is contacted. In addition, as illustrated in FIG. 8, a wire traction mechanism 50 is connected to the proximal end side of the bending lever 45 inside the operation section 3. Further, respective traction wires 23 are connected to the wire traction mechanism 50 through an intermediate lever mechanism 60. The bending lever 45, the wire traction mechanism 50, and the intermediate lever mechanism 60 configure a bending operation device 70 that bends the bending portion 7 in an optional direction.

As illustrated in FIGS. 5 to 8, the wire traction mechanism 50 includes: a housing 51; a rotary frame 52 that is pivotally (swingably) supported in the housing 51; a base member 53 that is pivotally (swingably) supported in the rotary frame 52; and a wire traction member 54 that is fixed to the base member 53.

The housing 51 is configured of a member that has a substantially cylindrical shape, and shaft holes 51a that face each other are bored in a peripheral wall of the housing 51.

The rotary frame 52 is configured of, for example a frame body that has a substantially rectangular shape. Paired screw holes 52a that face each other are bored at respective centers of both end parts of the rotary frame 52 in a longitudinal direction, and paired shaft holes 52b that face each other are bored at respective centers of both end parts of the rotary frame 52 in a short direction. In addition, screws 55 that are respectively inserted into the shaft holes 51a of the housing 51 are respectively screwed into the screw holes 52a, which causes the rotary frame 52 to be pivotally supported with respect to the housing 51.

The base member 53 is configured of a member having a substantially pillar shape. The bending lever 45 is integrally provided on a center axis of the base member 53. In addition, paired flat parts 53b that face each other are provided on a peripheral part of the base member 53, and a screw hole 53c that penetrates the flat parts 53b is bored. The screws 56 that are respectively inserted into the shaft holes 52b of the rotary frame 52 are screwed into the screw hole 53c, which causes the base member 53 to be pivotally supported with respect to the rotary frame 52. Further, the base member 53 is supported by the housing 51 through the rotary frame 52 in such a manner as to allow the bending lever 45 that is integrally connected to the base member 53 to be inclined in an optional direction.

The wire traction member 54 is configured of a plate member from which arm parts 54b are extended in four directions different from one another. In the present embodiment, more specifically, the wire traction member 54 is configured of a cross-shaped plate member in which an angle formed by the arm parts 54b adjacent to each other is set to 90 degrees. A center part 54a of the wire traction member 54 is fixed to the base member 53 through screws 57. In other words, the bending lever 45 is coupled to the wire traction member 54 through the base member 53, which allows the distal ends of the respective arm parts 54b to be displaceable in conjunction with the inclination operation of the bending lever 45. In addition, a wire fixing hole 54c is bored in the distal end of each of the arm parts 54b that are displaceably supported. Note that the angle formed by the arm parts 54b is not limited to 90 degrees, and may be optionally varied within a range of plus/minus 30 degrees from 90 degrees.

The wire traction mechanism 50 having the above-described configuration is so disposed as to face the cylinder 43 in front-rear direction in the operation section body 32. In this case, the wire traction mechanism 50 is disposed at a position at which each of the arm parts 54b is rotated around a center axis OI of the bending lever 45 within a range of 30 degrees to 60 degrees (for example, at a position at which each of the arm parts 45b is rotated by 45 degrees) with respect to the up-down/right-left inclination directions that are defined for the bending lever 45. Accordingly, for example, as illustrated in FIG. 4, the wire traction mechanism 50 is disposed in a state in which the cylinder 43 is placed between the two arm parts 54b of the wire traction member 54.

As illustrated in FIGS. 8 and 9, the intermediate lever mechanism 60 includes: right and left paired stays 61 that are extended from the inside of the operation section body 32 to the inside of the grasping portion 33; and four intermediate levers 62 that are supported by the stays 61.

The intermediate levers 62 are arranged side by side inside the grasping portion 33, and respective fixed ends of the intermediate levers 62 are swingably supported with, as a fulcrum, a single shaft portion 63 that is provided between the right and left stays 61.

The intermediate levers 62 respectively correspond to the arm parts 54b of the wire traction mechanism 50. A force point 62a to which a displacement amount of each of the arm parts 54b associated with the inclination operation of the bending lever 45 is transferred through an intermediate wire 65 is set in a middle of each of the intermediate levers 62. Further, a point of application 62b that amplifies the displacement amount of each of the arm parts 54b to transfer the amplified displacement amount to each of the traction wires 23 is set on a free end of each of the intermediate levers 62. The free end is located at a position farther from the fulcrum (the shaft portion 63) than the force point 62a.

More specifically, for example, as illustrated in FIGS. 8 and 9, the wire fixing hole 54c of each of the arm parts 54b is connected to a proximal end of the corresponding intermediate wire 65. In contrast, a first screw wire adjusting portion 66 to adjust the length of the intermediate wire 65 is provided on the force point 62a of each of the intermediate levers 62, and the distal end of the intermediate wire 65 is connected to the corresponding intermediate lever 62 through the first wire adjusting portion 66. Further, a pulley 68 that is supported by the operation section body 32 engages with the middle of each of the intermediate wires 65.

Further, the proximal end of each of the intermediate wires 65 is so adjusted as to be directed, at an angle within a predetermined angle range to the perpendicular direction of the corresponding arm part 54b (for example, at an angle within an error range of plus/minus about 20 degrees with respect to a perpendicular direction of the corresponding arm part 54b) when the bending lever 45 is in a neutral state, through setting of the position of the corresponding pulley 68, etc. Further, the distal end of each of the intermediate wires 65 is so adjusted as to be directed, at an angle within a predetermined angle range to the perpendicular direction of the corresponding intermediate lever 62 (for example, at an angle within an error range of plus/minus about 20 degrees with respect to a perpendicular direction of the corresponding intermediate lever 62) when the bending lever 45 is in the neutral state, through setting of the position of the corresponding pulley 68, etc.

Moreover, for example, as illustrated in FIGS. 8 and 9, a second screw wire adjusting portion 67 to adjust the length of the corresponding traction wire 23 is provided at the point of application 62b of each of the intermediate levers 62, and the proximal ends of the respective traction wires 23 are respectively connected to the intermediate levers 62 through the second wire adjusting portions 67. Note that the distal ends of the respective traction wires 23 are arranged in the insertion section 2 while being crossed in up-down/right-left directions.

In such a configuration, for example, when a user or the like grasps the grasping portion 31 of the operation section 3 and inclines the bending lever 45 in the left inclination direction by a thumb of the grasping hand, the intermediate wires 65 that are respectively coupled to the two arm parts 54b located in the right inclination direction are mainly pulled. The traction of the intermediate wires 65 are transferred to the corresponding intermediate levers 62, and the respective intermediate levers 62 swing at the angle corresponding to the traction amount. As a result, in the bending portion 7, the two traction wires 23 located on the left side in the bending direction are mainly pulled with the traction amount amplified by the corresponding intermediate levers 62, and the bending portion 7 is accordingly bent leftward.

In addition, for example, when the user or the like grasps the grasping portion 31 of the operation section 3 and inclines the bending lever 45 in the right inclination direction by the thumb of the grasping hand, the intermediate wires 65 that are respectively coupled to the two arm parts 54b located in the left inclination direction are mainly pulled. The traction of the intermediate wires 65 are transferred to the corresponding intermediate levers 62, and the respective intermediate levers 62 swing at the angle corresponding to the traction amount. As a result, in the bending portion 7, the two traction wires 23 located on the right side in the bending direction are mainly pulled with the traction amount amplified by the corresponding intermediate levers 62, and the bending portion 7 is accordingly bent rightward.

In addition, for example, when the user or the like grasps the grasping portion 31 of the operation section 3 and inclines the bending lever 45 in the up inclination direction by the thumb of the grasping hand, the intermediate wires 65 that are respectively coupled to the two arm parts 54b located in the down inclination direction are mainly pulled. The traction of the intermediate wires 65 are transferred to the corresponding intermediate levers 62, and the respective intermediate levers 62 swing at the angle corresponding to the traction amount. As a result, in the bending portion 7, the two traction wires 23 located on the lower side in the bending direction are mainly pulled with the traction amount amplified by the corresponding intermediate levers 62, and the bending portion 7 is accordingly bent upward.

In addition, for example, when the user or the like grasps the grasping portion 31 of the operation section 3 and inclines the bending lever 45 in the down inclination direction by the thumb of the grasping hand, the intermediate wires 65 that are respectively coupled to the two arm parts 54b located in the up inclination direction are mainly pulled. The traction of the intermediate wires 65 are transferred to the corresponding intermediate levers 62, and the respective intermediate levers 62 swing at the angle corresponding to the traction amount. As a result, in the bending portion 7, the two traction wires 23 located on the upper side in the bending direction are mainly pulled with the traction amount amplified by the corresponding intermediate levers 62, and the bending portion 7 is accordingly bent downward.

According to such an embodiment, the bending operation device 70 includes: the bending lever 45 that is inclinably supported with respect to the operation section 3 of the endoscope 1; the arm part 54b that is provided in the bending lever 45 and has the distal end displaceable in conjunction with the inclination operation of the bending lever 45; and the intermediate lever 62 that is swingably supported with respect to the operation section 3, has the force point 62a to which the distal end of the arm part 54b is connected through the intermediate wire 65, and has the point of application 62b to which the bending wire 23 is connected, at the position farther from the fulcrum (the shaft portion 63) than the force point 62a. This makes it possible to bend the bending portion 7 at a sufficient bending angle without enlarging the arm part 54b.

In other words, the displacement amount (the traction amount) by the arm part 54b is amplified by the intermediate lever 62 and the amplified displacement amount is transferred to the traction wire 23, which makes it possible to bend the bending portion 7 with the sufficient traction amount without enlarging the arm part 54b. Accordingly, it is possible to prevent interference between the arm part 54b and other built-in devices, and to efficiently suppress enlargement of the operation section 3 as well.

In this case, the pulley 68 that engages with the middle of the intermediate wire 65 is provided and the proximal end of the intermediate wire 65 when the bending lever 45 is in the neutral state is so set by the pulley 68 as to be directed substantially perpendicular to the arm part 54b. This makes it possible to efficiently convert the displacement amount of the arm part 54*b* into the traction amount of the intermediate wire 65. In addition, the distal end of the intermediate wire 65 when the bending lever 45 is in the neutral state is so set by the pulley 68 as to be directed substantially perpendicular to the intermediate lever 62. This makes it possible to efficiently convert the traction amount of the intermediate wire 65 into the swing amount of the intermediate lever 62.

Moreover, the stays 61 are extended from the operation section body 32 side to the grasping portion 33 side, and the intermediate levers 62 that amplify the traction amount of the respective arm parts 54*b* are provided in the grasping portion 33. This allows for effective use of the dead space in the operation section 3. In addition, the respective intermediate levers 62 are arranged on the single shaft portion 63 and are pivotally supported, which allows for collective arrangement of the intermediate levers 62 in one place.

Further, the first wire adjusting portions 66 that respectively adjust the lengths of the intermediate wires 65 connected to the force points 62*a* of the respective intermediate levers 62 and the second wire adjusting portions 67 that respectively adjust the lengths of the traction wires 23 connected to the points of application 62*b* of the respective intermediate levers 62 are provided in the intermediate lever mechanism 60. This makes it possible to easily tune the relationship between the inclination state of the bending lever 45 and the bent state of the bending portion 7. In other words, the intermediate lever mechanism 60 according to the present embodiment including the first and second wire adjusting portions 66 and 67 roughly adjusts the relationship between the inclination state of the bending lever 45 and the bent state of the bending portion 7 through the length adjustment of the intermediate wires 65 by the respective first wire adjusting portions 66, and then finely adjusts the above-described relationship through the length adjustment of the traction wires 23 by the respective second wire adjusting portions 67. This facilitates the tuning work. In this case, in particular, collectively providing the respective intermediate levers 62 in the grasping portion 33 and providing the first and second wire adjusting portions 66 and 67 while being coupled to the force points 62*a* and the points of application 62*b* of the respective intermediate levers 62 allow for easy access to all of the wire adjusting portions 66 and 67 through simple work of detaching the grasping portion 33 from the operation section body 32 without disassembly or other work of the operation section body 32.

Note that the present invention is not limited to the embodiment described above, and may be variously modified and altered. The modification and the alteration are also within the technical scope of the present invention.

What is claimed is:

1. A bending operation device, comprising:
    a bending lever that is inclinably supported with respect to an operation section of an endoscope;
    an arm part that is provided on the bending lever and includes a distal end displaceable in conjunction with inclination operation of the bending lever; and
    an intermediate lever, wherein
    the intermediate lever includes a fixed end and a free end that are set on both ends in a longitudinal direction of the intermediate lever, the fixed end being swingably supported with respect to the operation section via a fulcrum, the intermediate lever further includes a force point between the fixed end and the free end and a point of application at a position on the intermediate lever that is farther from the fulcrum than the force point and is closer to the free end than the force point, the force point being connected to the distal end of the arm part through an intermediate wire, the point of application being connected to a bending wire, and the bending wire bending a bending portion provided in an insertion section of the endoscope.

2. The bending operation device according to claim 1, further comprising a pulley that engages with a middle of the intermediate wire and causes a proximal end of the intermediate wire when the bending lever is in a neutral state to be directed, at an angle within a predetermined angle range, to a perpendicular direction of the arm part.

3. The bending operation device according to claim 2, wherein the pulley causes a distal end of the intermediate wire when the bending lever is in the neutral state to be directed, at an angle within a predetermined angle range, to a perpendicular direction of the intermediate lever.

4. The bending operation device according to claim 1, further comprising:
    a first wire adjusting portion that adjusts a length of the intermediate wire connected to the force point of the intermediate lever; and
    a second wire adjusting portion that adjusts a length of the bending wire connected to the point of application of the intermediate lever.

5. An endoscope comprising:
    an operation section;
    an insertion section connected to a distal end of the operation section; and
    a bending operation device located in the operation section, the bending operation device comprising;
        a bending lever that is inclinably supported with respect to the operation section,
        an arm part that is provided in the bending lever and includes a distal end displaceable in conjunction with an inclination operation of the bending lever; and
        an intermediate lever,
    wherein the intermediate lever includes a fixed end and a free end that are set on both ends in a longitudinal direction of the intermediate lever, the fixed end being swingably supported with respect to the operation section via a fulcrum, the intermediate lever further includes a force point between the fixed end and the free end and a point of application on the intermediate lever at a position that is farther from the fulcrum than the force point and is closer to the free end than the force point, the force point being connected to the distal end of the arm part through an intermediate wire, the point of application being connected to a bending wire, and the bending wire bending a bending portion provided in an insertion section of the endoscope.

* * * * *